United States Patent [19]

Finegold

[11] Patent Number: 4,460,360
[45] Date of Patent: Jul. 17, 1984

[54] URETHRAL ANESTHETIC DEVICES

[76] Inventor: Aaron N. Finegold, 136 Beechwood La., Pittsburgh, Pa. 15206

[21] Appl. No.: 525,989

[22] Filed: Aug. 24, 1983

Related U.S. Application Data

[62] Division of Ser. No. 412,985, Aug. 30, 1982, Pat. No. 4,432,758.

[51] Int. Cl.³ .............................................. A61F 15/00
[52] U.S. Cl. ..................................................... 604/288
[58] Field of Search ........................ 604/288, 285, 239

[56] References Cited

U.S. PATENT DOCUMENTS

| | | | |
|---|---|---|---|
| 467,599 | 1/1902 | Abundi et al. | |
| 794,233 | 7/1905 | Kistler | 604/288 |
| 1,767,785 | 6/1930 | DeSushko | 604/288 |
| 2,072,438 | 3/1937 | Ackerman | 128/271 |
| 3,335,725 | 8/1967 | Gordon | 128/261 |
| 3,537,454 | 11/1970 | Gordon | 128/261 |
| 3,570,489 | 3/1971 | Brown | 128/275 |
| 3,690,316 | 9/1972 | Haller | 128/130 |
| 3,927,672 | 12/1975 | FeGarcia | 128/245 |

FOREIGN PATENT DOCUMENTS 1260373 12/1961 France ................................ 604/288

Primary Examiner—John D. Yasko
Attorney, Agent, or Firm—Webb, Burden, Robinson & Webb

[57] ABSTRACT

Instruments for anesthetizing the urethra of male and female patients are disclosed.

The male instrument includes a standard syringe with an elongated hollow barrel mounted on the syringe. The barrel is formed in the shape of a Van Buren curve and includes one or more openings near its tip. The male instrument also includes a meatal obstructor slidably mounted around the barrel. The barrel is adapted to be inserted into the entire length of a patient's urethra and is then withdrawn while simultaneously applying an anesthetic through the openings and maintaining the obstructor against the external orifice of the urethra.

The female instrument includes a solid anesthetic suppository attached to one surface of a meatal obstructor and a handle attached to another surface of the obstructor. The suppository is formed in the shape of an anatomical female infrapubic curve. The suppository is inserted into the urethra and anesthetizes the entire urethra as the suppository dissolves.

4 Claims, 5 Drawing Figures

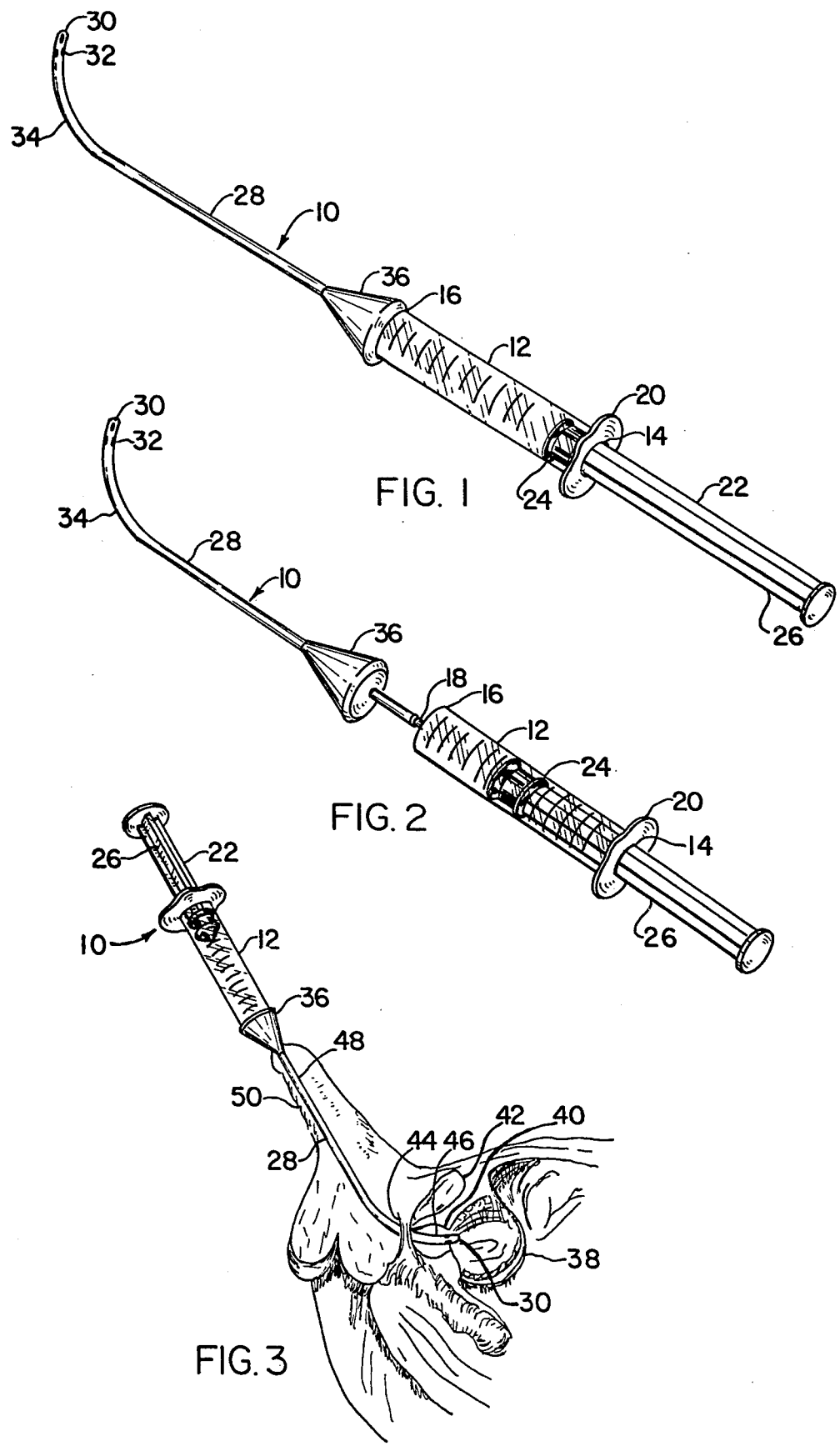

URETHRAL ANESTHETIC DEVICES

This application is a division of application Ser. No. 412,985, filed Aug. 30, 1982 now U.S. Pat. No. 4,432,758.

DESCRIPTION

1. Field of the Invention

This invention relates to anesthetic devices and, more particularly, to instruments for applying a local or topical anesthetic to the urethra of male and female patients.

2. Background Art

A patient undergoing a procedure which includes manipulation of the urethra, such as a treatment, dilatation, cystoscopy and the like, is often placed under a general anesthetic. However, a general anesthetic is dangerous for many patients because of the patient's age or physical condition and a local anesthetic is preferable. Also, if urethral treatment is performed in a physician's office, application of a local anesthetic to just the urethra is preferable to a general anesthetic.

In a presently used method of applying a local anesthetic to the urethra, a syringe filled with an anesthetic solution or jelly is placed adjacent the external orifice of the patient's urethra and the anesthetic is injected into this orifice and forced into the urethra under extreme pressure. Such a method causes discomfort, pain, and bleeding to the patient, and frequently the bleeding continues after the urethral treatment is completed. In addition, the anesthetic injected in this manner does not travel the entire length of the urethra and leaves the posterior portions of the urethra without any anesthetic. This is a particular problem in male patients because of the length of the urethra and the presence of a restricting urethral sphincter muscle on the side of the prostrate gland opposite the bladder.

It is an object of the present invention to overcome these disadvantages and provide a urethral anesthetic application instrument which is safe and comfortable to the patient and which will anesthetize the entire length of the patient's urethra.

SUMMARY OF THE INVENTION

This invention includes instruments for applying a local or topical anesthetic to the entire urethra of male and female patients.

An instrument suitable for use in male patients includes a hollow syringe body with a first end which is open to the atmosphere and a second end which terminates in a coupler in fluid communication with the interior of the syringe body, a slidable plunger assembly disposed within the syringe body and extending through the first end, an elongated hollow barrel connected to the coupler and including a passageway in fluid communication with the coupler, and a meatal obstructor slidably mounted around the barrel. The barrel is formed in the shape of the interior of the male urethra with a Van Buren curve and includes one or more openings adjacent the end of the barrel opposite the coupler in communication with the passageway. The barrel is inserted into the entire length of a patient's urethra and then slowly withdrawn while simultaneously applying an anesthetic to the urethra through the openings by gradually depressing the plunger in the syringe body. The obstructor is positioned against the external orifice of the urethra while the barrel is withdrawn to prevent the anesthetic from escaping from the urethra. The obstructor is preferably cone-shaped, with the base of the cone directed toward the syringe body and with the barrel passing along the axis of the cone.

An instrument suitable for use in female patients includes a meatal obstructor with one flat surface, preferably a flat disc, a solid anesthetic suppository attached to and extending from the flat surface of the obstructor, and a handle attached to and extending from the other surface of the obstructor. The suppository is formed in the shape of the interior of the female urethra with an anatomical female infrapubic curve, and has a length substantially equal to the length of a patient's urethra. The suppository is inserted into the patient's urethra and anesthetizes the entire urethra as it is dissolved by the patient's body heat.

BRIEF DESCRIPTION OF THE DRAWINGS

FIG. 1 is a perspective view of a urethral anesthetic application instrument in accordance with one embodiment of the present invention, FIG. 2 is a perspective view of the instrument shown in FIG. 1 in a second configuration;

FIG. 3 is a cross-sectional view of a portion of the male anatomy with the barrel of the instrument shown in FIG. 1 inserted into the urethra;

DESCRIPTION OF THE PREFERRED EMBODIMENTS

Figure 4:
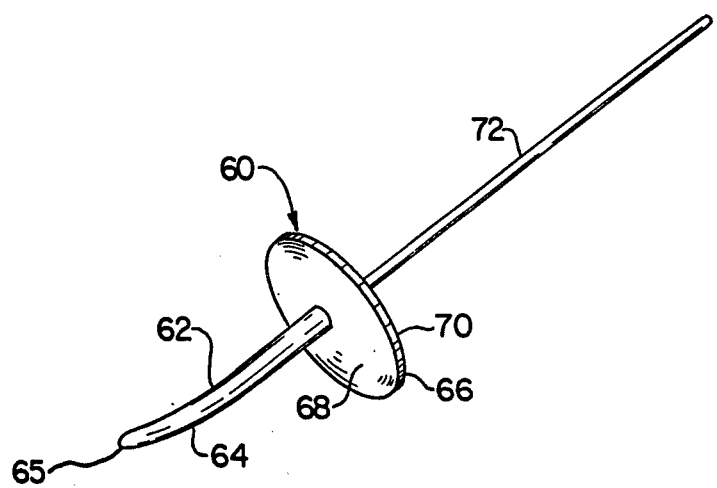
FIG. 4 is a perspective view of a urethral anesthetic application instrument in accordance with a second embodiment of the present invention.

A urethral anesthetic application instrument in accordance with the present invention is shown in FIGS. 1–3. This instrument is particularly useful in anesthetizing a male patient's urethra and is referred to as a male anesthetic instrument 10.

The male instrument 10 includes an elongated hollow, preferably tubular, syringe body 12 with a first end 14 which is open to the atmosphere, a second end 16 which terminates in a coupler 18, and a handle 20 extending outwardly from syringe body 12 at first end 14. The coupler 18 is a short hollow tube in fluid communication with the interior of syringe body 12 and may be externally threaded at its free end.

A slidable plunger assembly 22 is disposed within syringe body 12 and extends through first end 14 of syringe body 12. The plunger assembly 22 includes a piston portion 24, preferably made of an elastomeric rubber, which remains inside of and in contact with the interior of syringe body 12, and a stem portion 26 connected to piston portion 24 and extending out of syringe body 12 through first end 14.

An elongated hollow barrel 28 having a smooth exterior surface is connected to the free end of coupler 18 and includes a central passageway in fluid communication with coupler 18 and with the interior of syringe body 12. The tip 30 of barrel 28, which is the end furthest from coupler 18, is solid and preferably rounded. The barrel 28 has one or more substantially radial openings 32 adjacent to tip 30. The openings 32 are located near, but not on, the tip 30 of barrel 28 and are in fluid communication with the central passageway through barrel 28. The barrel 28 is formed according to the shape of the interior of a male urethra with a Van Buren curve 34 to accommodate the internal curvature of the urethra. The barrel 28 must be of sufficient length to extend the entire distance between the external orifice of the urethra and the posterior urethra where the urethra joins the bladder. This length is typically between 6½ and 7½ inches for a male urethra. The barrel 28 should be approximately 8 to 10 french units in diameter (1 french unit=⅓ mm.) and the size of openings 32 should be no greater than 1 mm.

A meatal obstructor 36 is slidably mounted around barrel 28. The obstructor 36 is solid and cone-shaped, with the base of the cone directed toward the second end 16 of syringe body 12 and with barrel 28 passing through obstructor 36 along the axis of the cone. The obstructor 36 is shown in FIG. 1 in its initial position adjacent syringe body 12. The obstructor 36 may be manually moved along barrel 28 toward tip 30 and away from syringe body 12, as shown in FIG. 2.

The use of anesthetic instrument 10 in anesthetizing a male urethra is shown in FIG. 3. FIG. 3 shows the bladder 38, prostrate gland 40, pubic symphysis 42, pelvic diaphragm 44, posterior urethra 46, and anterior urethra 48 of a male patient. The syringe body 12 contains a suitable anesthetic, such as a lidocaine hydrochloride solution or jelly. The barrel 28 is inserted into the anterior urethra 48, past the sphincter muscle of the pelvic diaphragm 44, and through the posterior urethra 46 until the tip 30 just reaches the patient's bladder 38. The meatal obstructor 36 is positioned against the external orifice of the urethra on the meatus of the patient's penis 50. Then the anesthetic is slowly forced out of barrel 28 through openings 32 by gradually depressing plunger assembly 22 in syringe body 12, and the barrel 28 is simultaneously slowly withdrawn from the urethra. At the same time, obstructor 36 is maintained against the meatus of penis 50 and the barrel 28 is withdrawn through obstructor 36. As barrel 28 is withdrawn, the anesthetic is applied to the interior walls of first the posterior urethra 46 and then the anterior urethra 48 until the entire length of the urethra is anesthetized. The obstructor 36 is used to prevent the anesthetic from flowing out of the urethra during application. Once the entire barrel 28 has been withdrawn from the urethra, a spring clamp may be applied to the meatus of penis 50 to hold the anesthetic in the urethra until the urethra is sufficiently anesthetized, typically for one or two minutes. In this manner, the anesthetic is applied evenly and painlessly throughout the entire urethra with a minimum of discomfort to the patient.

The syringe body 12 and the barrel 28 may be molded as a unitary structure from a stiff plastic material. The barrel 28 may be made in different lengths to accommodate various urethra lengths in patients, but is preferably made in a length sufficient to anesthetize the entire length of the urethra in most patients. The openings 32 should be less than one millimeter in diameter for an anesthetic jelly, and should be equivalent in size to an 18 or 20 gauge needle opening for a liquid anesthetic solution.

Figure 5:
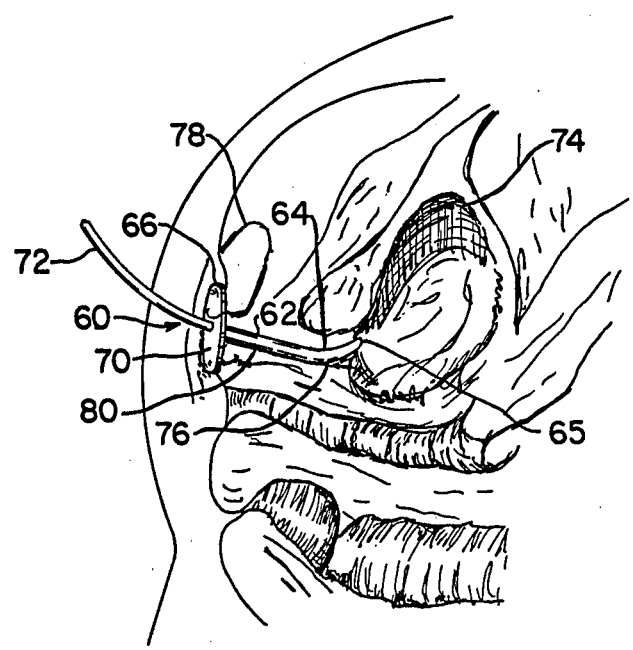
FIG. 5 is a cross-sectional view of a portion of the female anatomy with the suppository portion of the instrument shown in FIG. 4 inserted into the urethra.

A second urethral anesthetic application instrument in accordance with the present invention is shown in FIGS. 4 and 5. This instrument is particularly useful in anesthetizing a female patient's urethra and is referred to as a female anesthetic instrument 60.

The female instrument 60 includes a solid anesthetic suppository 62 which is formed in the shape of the interior of a female urethra with an anatomical female infrapubic curve 64 near rounded tip 65. This curve 64 is necessary because the female urethra bends obliquely downward and forward from the bladder. The suppository 62 is attached to a substantially flat surface of a meatal obstructor 66. The obstructor 66 is preferably a thin, flat disc substantially larger in diameter than suppository 62, with a pair of opposed flat surfaces 68 and 70. The suppository 62 may be attached to one of the flat surfaces, as shown in FIG. 4, surface 68. The female instrument 60 also includes a handle 72 attached to and extending away from the surface of obstructor 66 opposite from suppository 62, as shown, surface 70.

The suppository 62 is preferably an anesthetic solution in a base that dissolves at body temperature. One example of a suitable anesthetic solution is lidocaine hydrochloride. The suppository 62 must be of sufficient length to extend the entire distance along a patient's urethra, and be of sufficient diameter to have complete contact with the inner surface of the urethra. The typical length of a female urethra is 1 to 1½ inches. The diameter of the suppository 62 should be from 8 to 10 french units. The obstructor 66 and handle 72 may be formed as a unitary structure from a plastic material.

The use of anesthetic instrument 60 in anesthetizing a female urethra is shown in FIG. 5. FIG. 5 shows the bladder 74, bladder neck 76, pubic symphysis 78 and urethra 80 of a female patient. The suppository 62 is inserted into the entire length of the urethra 80 until the obstructor 66 touches the external orifice or the meatus of the urethra. The obstructor 66 prevents the tip 65 of suppository 62 from penetrating too far into the bladder 74. The suppository 62 is now in contact with the entire inner surface of the urethra 80 and begins to melt from the patient's body heat. The suppository 62 may be held in place by hand via the handle 72 or by a cotton pledget for a period of two to five minutes while the suppository melts and anesthetizes the urethra 80. The obstructor 66 also functions to prevent the anesthetic from draining out during the melting process. Once the urethra 80 is sufficiently anesthetized, the suppository 62, if any remains, is removed and the doctor may perform the desired treatment of the urethra 80.

Having described the preferred embodiments of the invention, it is to be understood that it may be otherwise embodied within the scope of the appended claims.

I claim:

1. Apparatus for applying a local anesthetic to the interior of a patient's urethra comprising:
   (a) a meatal obstructor with one substantially flat surface;
   (b) an elongated solid anesthetic suppository attached to and extending outwardly from said flat surface of said meatal obstructor, said suppository formed in the shape of an anatomical female infrapubic curve and said suppository having a length substantially equal to the length of the patient's urethra; and
   (c) a handle attached to another surface of said obstructor opposite said flat surface and extending outwardly therefrom, whereby said suppository may be inserted into the patient's urethra and thereby anesthetize the entire urethra as said suppository is dissolved by the patient's body heat.

2. The instrument of claim 1 wherein said suppository is an anesthetic solution in a base that dissolves at the patient's body temperature.

3. The instrument of claim 2 wherein said anesthetic solution is lidocaine hydrochloride.

4. The instrument of claim 1 wherein said meatal obstructor is a thin disc with a pair of opposed flat surfaces and wherein said suppository is attached to one of said opposed flat surfaces and said handle is attached to the other of said opposed flat surfaces.

* * * * *